US008142768B2

(12) United States Patent
Hagura et al.

(10) Patent No.: US 8,142,768 B2
(45) Date of Patent: Mar. 27, 2012

(54) COSMETIC PREPARATION

(75) Inventors: Toyoki Hagura, Tokyo (JP); Keigo Kajiwara, Tokyo (JP); Takashi Hori, Tokyo (JP); Satoshi Tsunakawa, Cincinnati, OH (US); Tetsuji Kito, Wakayama (JP)

(73) Assignee: Kao Corporation, Tokyo (JP)

(*) Notice: Subject to any disclaimer, the term of this patent is extended or adjusted under 35 U.S.C. 154(b) by 1029 days.

(21) Appl. No.: 11/137,493

(22) Filed: May 26, 2005

(65) Prior Publication Data

US 2005/0266057 A1 Dec. 1, 2005

(30) Foreign Application Priority Data

May 28, 2004 (JP) ................................. 2004-159671
Feb. 17, 2005 (JP) ................................. 2005-040554
Feb. 18, 2005 (JP) ................................. 2005-042029
Feb. 18, 2005 (JP) ................................. 2005-042030
Feb. 18, 2005 (JP) ................................. 2005-042239
Feb. 28, 2005 (JP) ................................. 2005-052431

(51) Int. Cl.
*A61K 8/81* (2006.01)
*A61F 13/00* (2006.01)
(52) U.S. Cl. ..................................... 424/70.16; 424/443
(58) Field of Classification Search .................. None
See application file for complete search history.

(56) References Cited

U.S. PATENT DOCUMENTS

| 4,962,133 | A | * | 10/1990 | Chromecek et al. | 521/56 |
| 6,063,366 | A | | 5/2000 | Sugai et al. | |
| 6,207,175 | B1 | | 3/2001 | Lebreton | |
| 6,262,170 | B1 | * | 7/2001 | Kilgour et al. | 524/731 |
| 6,312,672 | B1 | * | 11/2001 | Coolbaugh et al. | 424/59 |
| 6,531,113 | B1 | | 3/2003 | Mougin et al. | |
| 6,930,143 | B2 | * | 8/2005 | Harris et al. | 524/556 |
| 2002/0012682 | A1 | * | 1/2002 | Kashimoto | 424/401 |
| 2004/0096414 | A1 | * | 5/2004 | Mori et al. | 424/70.16 |
| 2005/0175650 | A1 | * | 8/2005 | Hadasch et al. | 424/401 |

FOREIGN PATENT DOCUMENTS

| EP | 0 950 391 A1 | 10/1999 |
| EP | 0950391 | * 10/1999 |
| EP | 1 400 233 A1 | 3/2004 |
| JP | 2000-1424 | 1/2000 |
| JP | 2000-186017 A | 7/2000 |
| JP | 2000186017 A | * 7/2000 |
| JP | 2000-302624 A | 10/2000 |
| JP | 2001-072887 | * 3/2001 |
| JP | 2001-106858 A | 4/2001 |
| JP | 2001-278736 A | 10/2001 |
| JP | 2002-265529 A | 9/2002 |
| JP | 2002-265620 | 9/2002 |
| JP | 2003-128827 | 5/2003 |
| JP | 2003-146826 | 5/2003 |
| JP | 2003-277417 | 10/2003 |
| JP | 2004-43557 | 2/2004 |
| JP | 2005-139322 | 6/2005 |
| JP | 2006-8659 | 1/2006 |
| JP | 2006-8757 | 1/2006 |
| JP | 2006-161027 | 6/2006 |

OTHER PUBLICATIONS

Machine-generated English translation of JP 2001-072887.*
An et al., Eur. Polym. J., 1997, 33(9), pp. 1523-1528.*
An et al., Eur. Polm. J., 1997, 33(9), pp. 1523-1528.*
Derwent Publications, AN 2001-341509, XP-002357106, JP 2001-106858, Apr. 17, 2001.
Derwent Publications, AN 2003-345550, XP-002357107, JP 2002-265529, Sep. 18, 2002.
Derwent Publications, AN 2001-237844, XP-002357108, JP 2000-302624, Oct. 31, 2000.
Derwent Publications, AN 2000-527865, XP-002357109, JP 2000-186017, Jul. 4, 2000.
Derwent Publications, AN 1998-515056, XP-002357110, JP 03-511455, Aug. 25, 1998.
European Notice of Opposition dated Oct. 18, 2010 in corresponding European Application No. 05 011 459.4.
Allured's Cosmetics & Toiletries Magazine, vol. 114, No. 6, Jun. 1999, p. 74.
Allured's Cosmetics & Toiletries Magazine, vol. 114, No. 12, Dec. 1999, p. 89.
Cosmetics & Toiletries Magazine, vol. 118, No. 1, Jan. 2003, p. 87.
Cosmetics & Toiletries Magazine, vol. 118, No. 7, Jul. 2003, p. 72.
Cosmetics & Toiletries Magazine, vol. 118, No. 12, Dec. 2003, p. 14.
Cosmetics & Toiletries Magazine, vol. 120, No. 1, Jan. 2005, p. 94.
BusinessDictionary.com, "compressive strength", © 2010, http://www.businessdictionary.com/definition/compressive-strength.html, Annex A.

* cited by examiner

*Primary Examiner* — Frederick Krass
*Assistant Examiner* — Brian Gulledge
(74) *Attorney, Agent, or Firm* — Oblon, Spivak, McClelland, Maier & Neustadt, L.L.P.

(57) ABSTRACT

The invention relates to a cosmetic preparation containing a crosslinked (meth) acrylic acid ester resin powder having a compression strength of 0.7 to 10 kgf/mm$^2$. The invention also relates to a cosmetic preparation, for example, in the form of a cosmetic sheet, powder spray cosmetic, gel cosmetic, two phase separable cosmetic, emulsion cosmetic or the like.

14 Claims, No Drawings

COSMETIC PREPARATION

FIELD OF THE INVENTION

The invention relates to a cosmetic preparation, which can be in the form of cosmetic sheet, powder spray cosmetic, gel cosmetic, two phase separable cosmetic, emulsion cosmetic or the like.

BACKGROUND OF THE INVENTION

Commercially available cosmetics containing a powder include makeup cosmetics such as foundation, face powder, rouge, and eye shadow; body cosmetic formulations such as body powder, baby powder, and body lotion; lotions such as face lotion and preshave lotion; as well as emulsions, creams, and the like. Powders are added to these cosmetics for the purpose of providing them with several functions, e.g., improving spreadability on the skin and the feeling thereof, concealing wrinkles, and the like.

Examples of the powders include inorganic powders such as silica and talc; and resin powders of polymethyl methacrylate, crosslinked polystyrene, nylon, polyethylene, and the like.

When applied on the skin, cosmetics containing an inorganic powder such as silica or talc or a resin powder can alleviate the greasy feeling and the shininess of the skin due to perspiration, sebum or oily components. Also they can improve the skin smoothness. But they can not obtain natural skin feeling because of the dry feeling inherent to the powder. Especially in a dry environment, for example, in winter, these cosmetics have not been favorable, as they provided dry feeling.

JP-A 2000-186017, JP-A 2000-302624 and JP-A 2002-265529 disclose external formulations containing crosslinked (meth)acrylic ester resin particles having a compression strength of 0.05 to 0.6 $kgf/mm^2$. These particles provide favorable spreadability and feelings, but still unsatisfactory. There exist a need for particles that are more easily spreadable and still provide such feelings as smoothness and softness.

On the other hand, various wet cosmetic sheets have been commercialized for use in wiping the body, for example, face, neck, hands and feet, and in shaving. There are a variety of such products, including products packed one by one, pocket tissue-type products containing ten or more sheets, and box-type products containing dozens to hundreds of sheets. These products are manufactured by impregnating appropriate sheets with cosmetic ingredients and other ingredients such as cleanser, tonic, bactericide, and perfume, and are used for cleansing the skin, refreshing the skin, or moisturizing the skin for shaving.

JP-A 2000-1424, equivalent to EP-A 950391, and JP-A 2001-278736 disclose cosmetic sheets impregnated with an inorganic powders such as silica or talc or a spherical powder such as organic silicone.

However, when the skin is wiped with these cosmetic sheets, the skin may become smoother with the powder, but the cosmetics leave the dry feeling of the powder on the user's skin, namely providing non-natural skin feeling. In addition, application of these powders may alleviate the sticky feeling caused by perspiration to some extent, but do not provide favorable feeling sufficiently when the skin condition is deteriorated or in dry seasons such as winter.

SUMMARY OF THE INVENTION

The invention provides a cosmetic preparation containing a crosslinked (meth) acrylic acid ester resin powder (a) having a compression strength of 0.7 to 10 $kgf/mm^2$.

The invention also provides a cosmetic sheet prepared by impregnating a sheet-shaped substrate with an aqueous dispersion containing the above mentioned component (a) and an oil, a powder spray cosmetic formulation containing the above mentioned component (a), a gel cosmetic containing the above mentioned component (a), a two phase separable cosmetic containing the above mentioned component (a) and a liquid medium, or an emulsion cosmetic containing the component (a). In addition, the invention relates to use of the crosslinked (meth) acrylic acid ester resin powder (a) having a compression strength of 0.7 to 10 $kgf/mm^2$ as a cosmetic ingredient.

The invention provides a cosmetic preparation that is softer and smoother and not greasy to the skin and does not make the skin shiny or dry, and can give a smooth feeling to the skin, and that retains the advantageous effects on such feelings for a prolonged period of time.

DETAILED DESCRIPTION OF THE INVENTION

Cosmetic Preparation

The component (a) according to the invention, a crosslinked (meth)acrylic acid ester resin powder having a compression strength of 0.7 to 10 $kgf/mm^2$, will be described below.

[Component (a)]

The resin powder of component (a) according to the invention preferably has a compression strength of 0.7 to 10 $kgf/mm^2$, in particular of 2 to 8 $kgf/mm^2$, for providing its favorable nonstickiness and smoothness.

The compression strength is a value calculated by the equation below, from the original particle size and the load applied for 10% decrease of the particle size during analysis of the resin particle in a compression test by using a micro compression testing machine MCT-M200 manufactured by Shimadzu Corporation. The compression strength is determined at 25° C. in said test.

$$\text{Compression strength } (kgf/mm^2) = 2.8 \times \text{load } (kgf)/(\pi \times \text{particle size (mm)} \times \text{particle size (mm)})$$

The compression strength of resin particle can be suitably controlled by adjusting the kinds and amounts of the monomer and the crosslinker for the resin particle.

The crosslinked (meth) acrylic acid ester resin powder for use in the invention is preferably a crosslinked (meth) acrylate ester resin powder prepared by copolymerization of the monomer components containing at least one monomer selected from acrylate and methacrylate esters (hereinafter, referred to as (meth)acrylate ester monomer) and a monomer having a carboxyl group. In the present specification, the "(meth)acryl" is a concept including both "acryl" and "methacryl".

The (meth) acrylate ester monomer for use in the invention is preferably an alkyl (meth)acrylate ester having an alkyl group of 1 to 18 carbon atoms. Typical examples thereof include methyl (meth)acrylate, ethyl (meth)acrylate, n-butyl (meth)acrylate, iso-butyl (meth)acrylate, 2-ethylhexyl (meth)acrylate, lauryl (meth)acrylate, stearyl (meth)acrylate, and the like. Among them, alkyl (meth)acrylates having an alkyl group of 4 to 18 carbon atoms such as butyl (meth)acrylate, lauryl (meth)acrylate, and stearyl (meth)acrylate are particularly preferable. These monomers may be used in combination of two or more. The content of the (meth) acrylate ester monomer in all monomer components (including the crosslinkable monomers described below; the same shall apply hereinafter) is preferably 30 to 98 weight % and more preferably 50 to 85 weight %.

Examples of the monomers having a carboxyl group for use in the invention include (meth)acrylic acid, maleic acid, fumaric acid, crotonic acid, itaconic acid, and the like. These monomers may be used in combination of two or more. The content of the monomer having a carboxyl group in all monomer components is preferably 0.1 to 30 weight % and more preferably 1 to 10 weight %, for the purpose of preventing aggregation of powders and providing the powder with favorable feelings (smoothness, nonstickiness).

Part of the carboxyl groups contained in the crosslinked (meth) acrylic acid ester resin powder may be neutralized. An inorganic base such as sodium hydroxide, potassium hydroxide, or ammonia is favorable as the base for neutralization, but an organic base such as amine, alkanolamine, or basic amino acid may be used instead. The neutralization degree is preferably 1 to 30% and particularly preferably 1 to 20% for improvement in the smoothness and the nonstickiness of powder. The neutralization degree is a ratio, in term of percent, of the mole number of a base added to the mole number of the carboxyl groups in the monomers having a carboxyl group.

The monomer components preferably contain a crosslinkable monomer having two or more vinyl groups as a crosslinker. Examples of the crosslinkable monomers include (meth)acrylic ester crosslinkable monomers such as ethylene glycol di(meth)acrylate, diethylene glycol di(meth)acrylate, triethylene glycol di(meth)acrylate, decaethylene glycol di(meth)acrylate, pentadecaethylene glycol di(meth)acrylate, 1,3-butylene glycol di(meth)acrylate, 1,4-butanediol di(meth)acrylate, 1,6-hexanediol di(meth)acrylate, glycerol di(meth)acrylate, allyl (meth)acrylate, trimethylolpropane tri (meth)acrylate, pentaerythritol tetra(meth)acrylate, phthalic acid diethylene glycol di(meth)acrylate, caprolactone-modified dipentaerythritol hexa(meth)acrylate, caprolactone-modified hydroxypivalic acid ester neopentylglycol di(meth) acrylate, polyester (meth)acrylate, and urethane (meth) acrylate; and aromatic divinyl monomers such as divinylbenzene, divinylnaphthalene and the derivatives thereof. These monomers may be used in combination of two or more. Among these crosslinkable monomers, (poly)alkylene glycol di(meth)acrylate such as ethylene glycol di(meth)acrylate, diethylene glycol di(meth)acrylate, triethylene glycol di(meth)acrylate, 1,3-butylene glycol di(meth)acrylate, 1,4-butanediol di(meth)acrylate, and 1,6-hexanediol di(meth) acrylate; caprolactone-modified dipentaerythritol hexa (meth)acrylates, caprolactone-modified hydroxypivalic acid ester neopentylglycol di(meth)acrylates, and polyester (meth)acrylates are preferable for use in the cosmetic preparation according to the invention because of their low skin irritability. These crosslinkable monomers are preferably used in an amount of 3 to 50 weight % with respect to all monomer components.

The monomer components may contain, in addition to the (meth)acrylate ester monomer, the monomer having a carboxyl group and the crosslinkable monomer, another monomer that is copolymerizable therewith. Examples of the other monomers include styrene, (meth)acrylonitrile, (meth)acrylamide, vinyl acetate, vinylpyrrolidone, and the like.

The crosslinked (meth) acrylic acid ester resin powder can be prepared, for example, by polymerizing the monomer components described above, containing the (meth)acrylate ester monomer, the monomer having a carboxyl group and the crosslinkable monomer by aqueous suspension polymerization, emulsion polymerization, seed polymerization, dispersion polymerization or the like by using a dispersant, a polymerization initiator and the like. Among the polymerization methods above, an aqueous suspension polymerization is preferable from the viewpoint of commercial scale production of the resin powders.

The aqueous. suspension polymerization is carried out by mixing an oil phase containing monomers and an aqueous phase and then heating the mixture while it is stirred. A surfactant is used as a dispersant. The amount of the surfactant is preferably 0.01 to 50 parts by weight, more preferably 0.01 to 10 parts by weight, and particularly preferably, 0.1 to 5 parts by weight with respect to 100 parts by weight of all monomer components.

The surfactant is favorably a surfactant having a sulfonic acid (salt) group. In this manner, it is preferably possible to prepare smooth and nonsticky resin powders.

Examples of the surfactants having a sulfonic acid (salt) group include those described in JP-A No. 2003-146826, paragraph numbers 0032 to 0036, and the like. Among them, alkyl or alkenyl ether sulfonic acids (or the salts thereof) having an alkyl or alkenyl group of 5 to 30 carbon atoms which may additionally contain 0.5 to 25 moles on average of added alkylene oxide in a molecule, and acylated taurines (or the salts thereof) having an alkyl or alkenyl group of 5 to 30 carbon atoms are preferable. Acylated taurines (salts) represented by the following General Formula (I) are particularly preferable.

$$R^1CONR^2CH_2CH_2SO_3M \qquad (I)$$

[wherein, $R^1$ represents an alkyl or alkenyl group having 5 to 30 carbon atoms which may be substituted; $R^2$ represents a hydrogen atom or a methyl group; and M represents a hydrogen atom or a cationic group.]

In General Formula (I), $R^1$ is preferably an alkyl or alkenyl group having 6 to 24 carbon atoms. Typical examples thereof include hexyl, octyl, nonyl, decyl, undecyl, dodecyl, tetradecyl, hexadecyl, octadecyl, eicosyl, docosyl, tetracosyl, decenyl, dodecenyl, tetradecenyl, hexadecenyl, octadecenyl, eicosenyl, and the like. Examples of the substituent groups of the alkyl or alkenyl group include hydroxyl group, carboxyl group, ester group, ether group, amide group, and the like.

Examples of the cationic group represented by M include alkali metals, ammonium, alkyl or alkenyl amines having a total carbon number of 1 to 22, alkanolamines having a total carbon number of 1 to 22, basic amino acid salts, and the like. Alkali metal ions such as lithium, sodium, and potassium are preferable; and a sodium ion is particularly preferable.

Examples of the polymerization initiators for use in polymerization include oil-soluble peroxides such as benzoyl peroxide, lauroyl peroxide, octanoyl peroxide, orthochlorobenzoyl peroxide, methylethylketone peroxide, diisopropyl peroxydicarbonate, cumene hydroperoxide, and t-butyl hydroperoxide; oil-soluble azo compounds such as 2,2'-azobisisobutylonitrile and 2,2'-azobis(2,4-dimethylvaleronitrile); and the like. The amount of the polymerization initiator added is preferably 0.1 to 10 weight % with respect to all monomer components.

The polymerization temperature and time are not particularly limited, but the polymerization temperature is preferably 40 to 100° C. and the polymerization time 1 to 15 hours.

The shape of the resin powder according to the invention is preferably spherical because it is more favorable in feel to the skin. In addition, the average particle size is preferably 1 μm or more, more preferably, 1.5 μm or more, and still more preferably 2 μm or more for reduction of squeaky feeling. On the other hand, it is preferably 10 μm or less, more preferably 8 μm or less, and particularly preferably 6 μm or less for prevention of roughness and improvement in skin fixing efficiency.

The average particle size can be determined by measuring a weight-average particle size with a laser diffraction particle size distribution analyzer (e.g., LA-920, manufactured by Horiba, Ltd.) by using an aqueous suspension of the powder at 20° C. at a relative refractive index of 1.1.

Cosmetic Sheet

The invention provides a cosmetic sheet, prepared by impregnating a sheet-shaped substrate with an aqueous dispersion containing the following components (a) and (b):
(a) Crosslinked (meth) acrylic acid ester resin powder having a compression strength of 0.7 to 10 kgf/mm²
(b) Oil.

The invention also provides a cosmetic sheet of which the aqueous dispersion optionally further contains a polymer dispersant as component (c) and a poly(N-acylalkyleneimine)-modified silicone as component (d).

The cosmetic sheet according to the invention provides the skin with a nonsticky and smooth feeling, and in addition, is superior in retaining the nonstickiness and smoothness to the skin.

The component (a) is the same as that described above.

[Component (b)]

Examples of the oil for use as component (b) of the invention include silicone oils, hydrocarbons, ester oils, aliphatic alcohols, ether oils, fatty acids, and the like.

Specifically, the silicone oils include dimethylpolysiloxane, diethylpolysiloxane, methylphenylpolysiloxane, methylhydrogenpolysiloxane, a copolymer of dimethylsiloxane and methylstearoxysiloxane, a copolymer of dimethylsiloxane and methylcetyloxysiloxane, cyclic polydimethylsiloxane, cyclic polymethylphenylsiloxane, cyclic polymethylhydrogensiloxane, fatty acid-modified polysiloxanes, higher alcohol-modified polysiloxanes, amino-modified polysiloxanes, epoxy-modified polysiloxanes; polyoxyalkylene-modified polysiloxane such as polyoxyethylene-methylpolysiloxanes, a copolymer of dimethylsiloxane and methyl (polyoxyethylene-polyoxypropylene)polysiloxane and a copolymer of dimethylsiloxane and methyl(polyoxypropylene)siloxane; alkoxy-modified polysiloxanes, long-chain alkyl-modified polysiloxanes and the like.

The hydrocarbons include squalane, petrolatum, liquid paraffin, and the like.

Examples of the ester oils include neopentylglycol dicaprate, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin, lanolin acetate, avocado oil, almond oil, olive oil, cacao oil, jojoba oil, sesami oil, safflower oil, soy bean oil, camellia oil, corn oil, wheat germ oil, peanut oil, turtle oil, apricot kernel oil, castor oil, mink oil, cottonseed oil, palm oil, egg yolk oil, polypropylene glycol monooleate, neopentylglycol-2-ethylhexanoate, isostearic acid triglyceride, myristic acid isostearic acid diglyceride, and the like.

Examples of the aliphatic alcohols include stearyl alcohol, cetostearyl alcohol, oleyl alcohol, and the like.

Examples of the ether oils include polyoxyethylene laurylethers, polyoxypropylene cetylether, and the like.

Examples of the fatty acids include oleic acid, stearic acid, isostearic acid and the like.

[Component (c)]

The polymer dispersant for use as component (c) of the invention is a water-soluble polymeric compound that facilitates dispersion of the components (a) and (b) in the aqueous medium. Examples thereof include carboxyvinyl polymers, alkyl-modified carboxyvinyl polymers, a copolymer of (meth) acrylic acid or a salt thereof and an alkyl (meth) acrylate, a copolymer of (meth)acrylic acid or a salt thereof, an alkyl (meth)acrylate and a (meth)acrylic acid polyoxyethylene alkylether and the like. These polymeric compounds function as a favorable thickener or dispersant when the carboxylic acid groups thereof are partially neutralized with a suitable base. The bases favorably used are inorganic bases such as sodium hydroxide, potassium hydroxide, sodium carbonate, and ammonia; alkanolamines such as triethanolamine, aminomethylpropanol, and diisopropanol amine; and the like.

[Component (d)]

The poly (N-acylalkyleneimine)-modified silicone for use as the component (d) of the invention include those having a poly(N-acylalkyleneimine) segment with a repeating unit represented by the following General Formula (II) that is bound via an alkylene group containing a hetero atom to at least one silicon atom at the end or in the main chain of the organopolysiloxane segment.

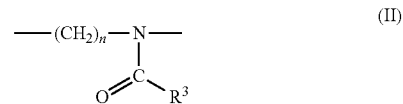

(wherein, R³ represents a hydrogen atom or an alkyl, cycloalkyl, aralkyl, or aryl group having 1 to 22 carbon atoms; and n is a number of 2 or 3.)

Said poly(N-acylalkyleneimine) segment can be obtained by a ring-opening polymerization of corresponding 2-oxazoline compound.

In General Formula (II), the cycloalkyl group represented by R³ is a cycloalkyl group having 3 to 6 carbon atoms; the aralkyl group being a phenylalkyl, a naphthylalkyl, or the like; the aryl group being phenyl, naphthyl, an alkyl-substituted phenyl, or the like. In addition, the alkylene group containing a hetero atom is, for example, an alkylene group having 2 to 20 carbon atoms and one to three atoms selected from nitrogen, oxygen, and sulfur.

A poly(N-acylalkyleneimine)-modified silicone having the poly(N-acylalkyleneimine) segment and the organopolysiloxane segment at a weight ratio of 1/50 to 20/1, preferably 1/40 to 2/1, and having a weight-average molecular weight of 500 to 500,000, preferably 1,000 to 300,000, is favorable for producing a cosmetic preparation comfortable in use, superior in powder dispersion, and effective in retaining the water and perspiration resistance, oil and sebum resistance, friction resistance, and the like thereof.

Favorable typical examples of the components (d) include those described in JP-A-9-202714, paragraph number 0021.

[Cosmetic Sheet]

The cosmetic sheet according to the invention can be prepared by impregnating a sheet-shaped substrate with an aqueous dispersion containing the components (a) and (b) and additionally the components (c) and (d) and others as needed.

The content of component (a) in the aqueous dispersion according to the invention is preferably 0.5 to 50 weight %, more preferably 1 to 30 weight %, and particularly preferably 1 to 15 weight % for providing a favorable nonstickiness to the skin and yet suppressing whitening of the skin.

The content of component (b) in the aqueous dispersion according to the invention is preferably 0.01 to 30 weight %, more preferably, 0.1 to 20 weight %, and particularly preferably, 0.1 to 10 weight % for providing a suitable oiliness.

When the aqueous dispersion according to the invention contains component (c) or component (d), the content of component (c) in the aqueous dispersion is preferably 0.01 to 2 weight %, more preferably 0.01 to 0.5 weight %, and particularly preferably 0.01 to 0.3 weight % for providing a favorable dispersion of the powder and feelings of the skin. Alternatively, the content of component (d) in the aqueous dispersion is preferably 0.05 to 10 weight % and more preferably 0.1 to 5 weight % for elongating the nonstickiness preservation.

The impregnation rate of the aqueous dispersion in the cosmetic sheet according to the invention is preferably 20 to 500 parts by weight and more preferably 50 to 400 parts by weight with respect to 100 parts by weight of the sheet-shaped substrate for improving feel upon use. The aqueous medium for the aqueous dispersion is preferably water or aqueous ethanol.

In the invention, any one of unwoven and woven fabrics of natural and synthetic fibers may be used as the sheet-shaped substrate. Typical examples thereof include woven or non-woven fabrics of rayon, acetate, acrylic, polyester, polyethylene, polypropylene, polyurethane, polyamide, cotton, or a mixture thereof; a wet- or dry-pulp sheet, a pulp sheet reinforced by a thermoplastic resin (polyethylene, polypropylene, polyethylene terephthalate or the like); and the like. Such a material is preferable because, the more densely the fibers are packed, the more powder can be present on the sheet surface. Pulp or cotton is particularly preferable as the substrate because of the easiness in processing during production. A laminate of multiple thin pulp sheets is preferable for well-balanced softness and strength, and a thermoplastic resin-reinforced pulp is also preferable as it provides a suitable thickness (bulkiness) by an embossing treatment and prevents the skin from becoming excessively wet. In addition, partial fastening of multiple sheets by heat sealing provides a sheet soft but tough enough for use in wiping while retaining a favorable impression upon use.

The cosmetic sheet according to the invention may additionally contain an alcohol such as ethanol, propylene glycol, 1,3-butanediol, glycerol, sorbitol, polyethylene glycol, or the like.

The cosmetic sheet according to the invention cleans the skin by removing the stains by perspiration and sebum when used for wiping the skin, and leaves the powder on the skin, which provides a nonsticky feeling and a smooth feeling without dryness effectively for a prolonged period of time.

In addition, a moisturizer, anti-inflammatory agent, whitening agent, UV-care agent, bactericide, antiperspirant, tonic, antioxidant, perfume, or the like may be additionally added to the cosmetic sheet according to the invention, for making these components remain on the skin with the powder, conditioning the skin efficiently after use and giving moisture, refreshment, and scent.

For example when used on the face, the cosmetic sheet according to the invention removes sebum effectively, preserves the skin in a favorable condition by leaving the powder and the moisturizer thereon, and makes the re-making up remarkably easier. When an antiperspirant and a bactericide are contained, the cosmetic sheet cleanses the skin and assures durable antiperspiration and deodorant effects by leaving these active ingredients on the skin for a prolonged period of time. The cosmetic sheet according to the invention is also useful in conditioning the skin after shaving when used in the areas of unwanted hair of the body. Namely, when applied on the skin prior to use of a razor, the cosmetic sheet moisturizes the areas, makes the razoring smooth by leaving the powder thereon, and conditions the skin in a favorable condition.

The cosmetic sheet according to the invention contains part of, preferably almost all of, the component (a) locally placed in the neighborhood of the surface of the substrate. The component (a) may be locally placed there, for example, by spraying or applying an aqueous dispersion containing both components (a) and (b) directly onto a sheet-shaped substrate. The cosmetic sheet according to the invention preferably contains the component (a) in the state that the cosmetic preparation can be easily applied onto the skin by a shearing force.

The cosmetic sheet according to the invention can be prepared by impregnating a sheet-shaped substrate with an aqueous dispersion containing components (a) and (b), and other components, for example, by spraying it by a spray or an air gun or coating it by using a slit nozzle or a bar coater. In particular, a preferable method of preparing a multifold cosmetic sheet product includes impregnating a single sheet-shaped substrate with the aqueous dispersion according to the invention by coating or spraying, cutting the sheet into pieces, and then piling up the pieces. Such a method can provide a product having powder uniformly distributed in each piece and exerting the advantageous effects of the invention more efficiently.

Powder Spray Cosmetic Formulation

The invention provides a powder spray cosmetic formulation containing a crosslinked (meth) acrylic acid ester resin powder having a compression strength of 0.7 to 10 kgf/mm$^2$.

The powder spray cosmetic formulation according to the invention provides the skin with a nonsticky and smooth feeling, and in addition, is superior in retaining the nonstickiness and smoothness to the skin.

The powder spray cosmetic formulation is an aerosol spray product mainly containing powdery components, which are applied on to the skin by spraying with a propellant and provide the sprayed area with the feelings of dryness, refreshment, smoothness, and the like. Powder spray cosmetic formulations are generally superior in dryness to gel or emulsion cosmetic preparations containing powdery components.

The powder spray cosmetic formulation according to the invention characteristically contains a crosslinked (meth) acrylic acid ester resin powder.

The crosslinked (meth) acrylic acid ester resin powder is the same as that described above.

The content of the crosslinked (meth)acrylic acid ester resin powder in the powder spray cosmetic formulation according to the invention is preferably 0.05 to 25 weight %, more preferably, 0.1 to 20 weight %, and still more preferably, 0.5 to 15 weight % with respect to the total amount of the powder spray including the propellant, for providing a favorable nonstickiness to the skin and yet suppressing the whitening of the skin.

The powder spray cosmetic formulation according to the invention may contain additionally an oil as needed. Examples of the oils include silicone oils, hydrocarbons, ester oils, aliphatic alcohols, ether oils, fatty acids, and the like.

Typical examples for the oils are the same as those exemplified for the component (b) of the cosmetic sheet.

The content of the oil in the powder spray cosmetic formulation according to the invention is preferably 0.001 to 30 weight %, more preferably 0.01 to 20 weight %, and particularly preferably, 0.01 to 10 weight % with respect to the total amount of powder spray preparation including the propellant, for providing a suitable oiliness.

The powder spray cosmetic formulation according to the invention preferably contains an antiperspirant. The antiperspirant is not particularly limited if it is a substance known to have an anti-perspiration action, and examples thereof include astringent salts of aluminum and zirconium such as aluminum halides, aluminum hydroxyhalides, zirconium oxyhalides, and zirconium hydroxyhalides or the astringent complexes thereof, and these antiperspirant may be used alone or in combination.

The content of the antiperspirant in the powder spray cosmetic formulation according to the invention is preferably 0.1 to 25 weight % and more preferably, 0.2 to 10 weight % with respect to the total amount of powder spray including the propellant, for providing a favorable anti-perspiration action to the skin and yet suppressing whitening of the skin.

In addition, the powder spray cosmetic formulation according to the invention preferably contains a bactericide. Examples of the bactericides include 3,4,4-trichlorocarbanilide, triclosan, benzalkonium chloride, benzethonium chloride, alkyltrimethylammonium chloride, resorcin, phenol, sorbic acid, salicylic acid, hexachlorophen, isopropylmethylphenol, and the like.

The content of the bactericide in the powder spray cosmetic formulation according to the invention is preferably 0.001 to 2 weight % and more preferably 0.05 to 1 weight % with respect to the total amount of powder spray including the propellant, for providing a favorable bactericidal action.

The powder spray cosmetic formulation according to the invention may contain additionally an alcohol such as ethanol, propylene glycol, 1,3-butanediol, glycerol, sorbitol, polyethylene glycol, or the like. It may also contain various compounds such as surfactant, moisturizer, anti-inflammatory agent, whitening agent, UV-care agent, oxidation inhibitor, tonic, and perfume in the range that does not impair the advantageous effects of the invention.

The powder spray cosmetic formulation according to the invention is prepared by filling the respective components and a suitable propellant in a sealed container equipped with an aerosol valve. The propellant for use in the invention is not particularly limited if it is a commonly used aerosol propellant, and examples thereof include liquefied petroleum gases such as propane, butane, and isopentane; halogenated hydrocarbons such as dichlorofluoromethane, 1,2-dichloro-1,1,2,2-tetrafluoroethane, and trichloromonofluoromethane; liquefied gases such as dimethylether; compressed gases such as carbon dioxide and nitrogen; and the like. The amount of the propellant used is preferably 45 to 98 weight % with respect to the total amount of powder spray cosmetic formulation according to the invention.

The powder spray cosmetic formulation according to the invention, when sprayed on the skin, leaves the active ingredients on the skin for a prolonged period of time and assures durable nonstickiness, antiperspiration and deodorant actions, and others.

Gel Cosmetic

The invention provides a gel cosmetic containing a crosslinked (meth)acrylic acid ester resin powder having a compression strength of 0.7 to 10 kgf/mm².

The gel cosmetics of the invention are cosmetics containing a liquid medium selected from water, lower alcohols, polyvalent alcohols, and others that is thickened with a thickener. The viscosity is preferably 3,000 mPa·s or more at 25° C. Such a cosmetic has a suitable viscosity when it is used and is thus easily applied onto the skin. The cosmetic allows stable dispersion of the powders and oily components in a viscous base substance and exhibits the advantageous properties of the added components effectively.

Hereinafter, each of the components for the gel cosmetic according to the invention will be described one by one.

The crosslinked (meth) acrylic acid ester resin powder is already described above.

[Gel-Forming Component]

As described above, gel cosmetic contains a liquid medium such as water, lower alcohol, polyvalent alcohol, or the like as the base substance that is thickened by a thickener.

Examples of the lower alcohols include alcohols having 1 to 4 carbons and typically, ethanol and iso-propanol are preferable, and ethanol is particularly preferable. Favorable examples of the polyvalent alcohols include glycerol, propylene glycol, 1,3-butanediol, and the like.

Water and these alcohols may be used as the liquid medium in combination, and the content of the liquid medium in the gel cosmetic according to the invention is preferably 30 to 97 weight % and more preferably 40 to 95 weight %, from the viewpoints of stability, dryness, refreshment, and non-greasy feeling.

Examples of the thickeners include carboxyvinyl polymers, acrylic acid/alkyl methacrylate copolymers, and the like, and the acrylic acid/alkyl methacrylate copolymers are particularly preferable. The acrylic acid/alkyl methacrylate copolymer is preferably a copolymer having the structure represented by the following Formula (III).

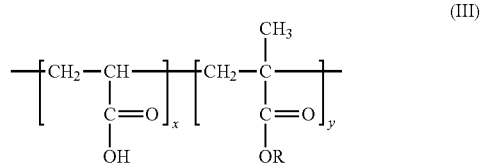

(wherein, R represents an alkyl group having 10 to 30 carbon atoms; x and y each represent the mol % of each unit in the copolymer; and x is 80 to 99.9 mol % and y is 0.1 to 20 mol %.) Such copolymers include commercial products such as PEMULEN TR-1, PEMULEN TR-2, and Carbopol ETD2020 manufactured by Noveon Inc.

A cellulosic polymer such as methylcellulose, ethylcellulose, hydroxyethylcellulose, hydroxypropylcellulose, or methylhydroxypropylcellulose may be used together with said vinyl polymer as the thickener.

The content of the thickener in the gel cosmetic according to the invention is preferably 0.05 to 2 weight % and more preferably, 0.1 to 1 weight %, from the viewpoint of thickening efficiency and application feeling such as nonstickiness and spreadability.

The gel cosmetic according to the invention, which characteristically contains the above mentioned crosslinked (meth)acrylic acid ester resin powder, may be applied as ultraviolet-protecting cosmetics, whitening cosmetics, deodorants, face and body moisturizing cosmetics and the like.

The content of the crosslinked (meth) acrylic ester resin powder in the gel cosmetic according to the invention is preferably 0.5 to 50 weight %, more preferably 1 to 30 weight %, and particularly preferably 1 to 15 weight %, for suppressing greasy feeling and whitening of the skin.

The gel cosmetic according to the invention is particularly useful as an ultraviolet-protecting cosmetic preparation containing an ultraviolet absorbent. Examples of the ultraviolet absorbents include ultraviolet absorbents derived from cinnamic acid, benzophenone, urocanic acid, benzoic acid, salicylic acid, benzoylmethane, triazine, anthranilic acid, and the like. Typical examples thereof include cinnamic acid ultraviolet absorbents such as benzyl paramethoxycinnamate, 2-ethylhexyl paramethoxycinnamate, 2-ethoxyethyl paramethoxycinnamate, diparamethoxycinnamic acid mono-2-ethylhexanoic acid glyceryl, and mixtures of isopropyl/diisopropyl paramethoxycinnamate; benzophenone ultraviolet absorbents such as hydroxymethoxybenzophenone, hydroxymethoxybenzophenonesufonic acid, sodium hydroxymethoxybenzophenonesufonate, dihydroxymethoxybenzophenone, sodium dihydroxymethoxybenzophenonedisulfonate, dihydroxybenzophenone, and tetrahydroxybenzophenone; urocanic acid ultraviolet absorbents such as urocanic acid and ethyl urocanate; benzoic acid ultraviolet absorbents such as paraminobenzoic acid, ethyl paraminobenzoate, glyceryl paraminobenzoate, amyl paradimethylaminobenzoate, octyl paradimethylaminobenzoate, and ethyl 4-[N,N-di(2-hydroxypropyl)amino]benzoate; salicylic acid ultraviolet absorbents such as ethylene glycol salicylate, phenyl salicylate, octyl salicylate, benzyl salicylate, p-tert-butylphenyl salicylate, and homomentyl salicylate; 4-tert-butyl-4'-methoxybenzoylmethane, oxybenzone, 2,4,6-tris [anilino-p-(carbo-2'-ethyl-1'-hexyloxy)]-1,3, 5-triazine, 2-(2-hydroxy-5-methylphenyl)benzotriazole, mentyl anthranilate, and the like, and among them, ultraviolet absorbents derived from cinnamic acid, benzoylmethane, and triazine are preferable from the point of stability. These ultraviolet absorbents may be used in combination of two or more.

The content of the ultraviolet absorbent in the gel cosmetic according to the invention is preferably 1 to 20 weight % and more preferably 2 to 10 weight %, from the viewpoints of non-sticky feeling to the skin and ultraviolet light-absorbing efficiency.

An ultraviolet light-scattering agent of inorganic powder may be added for further improvement of the ultraviolet-protecting efficiency. Examples of the ultraviolet light-scattering agents include titanium dioxide, zinc oxide, iron oxide, zirconium oxide, aluminum oxide, and the like, and the fine particles and complexes thereof. In particular, titanium dioxide and zinc oxide are preferable. The ultraviolet light-scattering agents may be used in combination of two or more, and the content is preferably 1 weight % or less, particularly preferably 0.5 weight % or less, from the point of stability.

The gel cosmetic according to the invention may additionally contain an oil, for adjustment of the feeling of cosmetic preparation. Examples of such oils include silicone oils, hydrocarbons, esteroils, aliphaticalcohols, etheroils, fatty acids, and the like.

Typical examples for the oils are the same as those exemplified for the component (b) of the cosmetic sheet.

In particular, ester oils and silicone oils are preferable for improvement in feeling. The content of the oil in the gel cosmetic according to the invention is preferably 0.1 to 10 weight % and more preferably, 0.1 to 5 weight %.

In addition to the components above, the gel cosmetic according to the invention may further contain other additives such as surfactant, whitening agent, bactericide, antiperspirant, moisturizer, tonic, perfume, and colorant in the range that does not impair the advantageous effects of the invention.

The gel cosmetic according to the invention is a formulation in which a crosslinked (meth)acrylic acid ester resin powder having a particular compression strength and the various components above are dispersed in a liquid medium that is thickened with a thickener. The content of water is preferably 10 to 68 weight % and more preferably, 12 to 55 weight % from the points of stability, unstickiness, and feelings after application such as refreshment.

The pH of the gel cosmetic according to the invention (at 25° C.) is preferably slightly acidic, i.e., 4 to 7, preferably 5 to 7, which is milder to the skin. When the liquid medium contains water in a greater amount, the pH can be measured as it is with a pH meter. When it contains a relatively smaller amount of water, pH of the gel cosmetic can be determined by diluting it, for example, 10 times with water and then measuring the pH of the resulting aqueous solution with a pH meter.

When applied on the skin, the gel cosmetic according to the invention suppresses the greasy feeling and dryness of the skin and elongates the period of these feelings to the skin. Further the gel cosmetic can retain the active ingredients such as ultraviolet light absorbent for an extended period of time.

Two Phase Separable Cosmetic

The invention provides a two phase separable cosmetic containing a crosslinked (meth) acrylic acid ester resin powder having a compression strength of 0.7 to 10 kgf/mm$^2$ and a liquid medium.

In the invention, two phase separable cosmetics are cosmetic preparations containing a powder suspended in a liquid medium selected from water, lower alcohols, polyvalent alcohols, and the like. In such a cosmetic, the powder precipitates when the cosmetic is allowed to stand resulting in a separation into two phases, liquid phase and solid phase. But the powder is easily re-dispersed into a suspension when shaken before use. Thus it is used in the suspended state for application on the skin.

Hereinafter, each of the components for the two phase separable cosmetic according to the invention will be described below one by one.

The crosslinked (meth) acrylic acid ester resin powder is already described above.

[Liquid Medium]

The liquid medium for use in the invention is, for example, at least one solvent selected from water, lower alcohols, and polyvalent alcohols; and a mixed solvent of water and a lower alcohol and/or a polyvalent alcohol is preferable. The ratio of water to alcohol, water/alcohol, is preferably 1/99 to 99/1 and more preferably, 5/95 to 95/5.

The lower alcohols for use in the invention include alcohols having 1 to 4 carbon atoms such as methanol, ethanol, and isopropyl alcohol; and ethanol is particularly preferable. Examples of the polyvalent alcohols include propylene glycol, 1,3-butylene glycol, glycerol, and the like.

It is possible to control the drying speed and skin feeling of the two phase separable cosmetic according to the invention by adjusting the composition of liquid medium, for example a ratio of water to alcohol, according to the desired properties of the product. It is also possible to dissolve effective components including oil such as ester oil, anti-inflammatory, ultraviolet absorbent, plant extract, and the like uniformly in a greater amount, by increasing the amount of alcohols used and thus to provide the cosmetic with the particular actions of these components.

[Two Phase Separable Cosmetic]

The two phase separable cosmetic according to the invention is favorably used as a shave lotion such as preshave or aftershave lotion, a face and body lotion for providing the skin stained by perspiration or sebum with refreshed feeling, a deodorant, a lotion for facilitating putting on and taking off gloves and stockings as applied on the hands and feet, and the like.

The two phase separable cosmetic according to the invention characteristically contains the crosslinked (meth)acrylic acid ester resin powder above. The content of the crosslinked (meth)acrylic acid ester resin powder is preferably 0.5 to 50 weight % and more preferably 1 to 30 weight %, for suppressing the greasy feeling and whitening of the skin and providing the skin with smoothness. The content is particularly preferably 1 to 15 weight %.

The content of the liquid medium in the two phase separable cosmetic according to the invention is preferably 50 to 99.5 weight %, more preferably 70 to 99 weight %, and particularly preferably 80 to 98 weight %.

The two phase separable cosmetic according to the invention may additionally contain, as needed, other powders including inorganic powders talc, titania, and the like in the range that does not impair the caking-resistance and stability thereof. In addition, the two phase separable cosmetic according to the invention may further contain, as needed, other additives commonly used in cosmetic such as surfactant, oil, tonic, anti-inflammatory, medicine, moisturizer, bactericide, antiperspirant, oxidation inhibitor, whitening agent, ultraviolet absorbent, perfume, and colorant in the range that does not impair the advantageous effects of the invention.

The two phase separable cosmetic according to the invention is prepared by mixing the crosslinked (meth) acrylic acid ester resin powder, the liquid medium, and other components as needed by conventional means, and is provided as a product as it is filled in a suitable container. Examples of the containers include bottles, roll-on containers, pump spray containers, aerosol containers, and the like.

The two phase separable cosmetic according to the invention suppresses the greasy feeling and dryness of the skin, facilitates the movement of shaver, assures the smoothness of the skin, and further provides these feelings for a longer period of time.

Emulsion Cosmetic

The invention provides an emulsion cosmetic containing a crosslinked (meth)acrylic acid ester resin powder having a compression strength of 0.7 to 10 kgf/mm$^2$.

The crosslinked (meth) acrylic acid ester resin powder is already described above.

The emulsion cosmetic according to the invention may be a water-in-oil (W/o) or oil-in-water (O/W) emulsion, and may include all kinds of cosmetics that are applied onto the skin as an emulsion. Examples thereof include cream, foundation, milky lotion, eye shadow, lip gloss, mascara, eye liner, and the like.

The emulsion cosmetic according to the invention characteristically contains the crosslinked (meth)acrylic acid ester resin powder above in an emulsion system.

The content of the crosslinked (meth)acrylic acid ester resin powder in the emulsion cosmetic according to the invention is preferably 0.5 to 50 weight %, more preferably 1 to 30 weight %, and particularly preferably 1 to 15 weight %, for suppressing the greasy feeling and whitening of the skin.

The oil contained in the oil phase of the emulsion cosmetic according to the invention is not particularly limited, and any one of the oils commonly used in cosmetic may be used. Examples thereof include silicone oils, hydrocarbons, ester oils, aliphatic alcohols, ether oils, fatty acids, and the like, and these oils may be used alone or in combination of two or more.

Typical examples for the oils are the same as those exemplified for the component (b) of the cosmetic sheet.

The content of the oil in the emulsion cosmetic according to the invention is preferably 0.1 to 20 weight and more preferably, 0.5 to 10 weight %, for suppressing the greasy feeling and providing a suitable oiliness.

The emulsion cosmetic according to the invention may contain water in any amount, but the content is preferably 10 weight % or more, more preferably 10 to 95 weight %, and particularly preferably 30 to 90 weight % with respect to the total amount with other water-soluble solvents, for improving feel upon use, i.e., for reducing the oily or greasy feeling and improving the applicability. Examples of the other water-soluble solvents include lower alcohols such as ethanol, isopropanol; and polyols such as glycerol, sorbitol, propylene glycol, and 1,3-butylene glycol.

The emulsion cosmetic according to the invention preferably contains an emulsifier. Examples of the emulsifiers include nonionic surfactants, for example, polyoxyethylene adduct type, polyglycerin esters, polyglycerin ethers, alkyl glycosides, and sugar esters; and the like.

The emulsion cosmetic according to the invention may contain, in addition to the components above, other additives such as thickener, moisturizer, ultraviolet absorbent, whitening agent, bactericide, oxidation inhibitor, tonic, and perfume in the range that does not impair the advantageous effects of the invention,

EXAMPLE

The present invention is described in more detail by reference to the Examples. The Examples are described for illustrative purposes only and not intended to limit the scope of the present invention.

"%" in the following Examples is weight %, unless otherwise indicated.

Preparation Example 1

82 g of lauryl methacrylate, 3 g of methacrylic acid, 15 g of ethylene glycol dimethacrylate, and 2 g of lauroyl peroxide were mixed and stirred in a beaker until dissolved. A solution of 0.75 g of sodium N-stearoyl-N-methyltaurine (SMT) in 400 g of ion-exchange water was added thereto, and the mixture was dispersed by using a homomixer until the particle size of oil droplet became 2.2 μm.

The dispersion was transferred into a four-necked flask, and the flask was purged and substituted with nitrogen for 30 minutes while the dispersion was stirred. The mixture in the flask was heated in an oil bath to a temperature of 80° C., allowed to polymerize at 80° C. for 5 hours, and then allowed to cool to room temperature. The polymerized particles were collected by freeze drying the dispersion, to give a resin powder A.

Preparation Example 2

A neutralized resin powder A was prepared in a similar manner to Preparation Example 1, except that the dispersion containing polymerized particles in Preparation Example 1 was neutralized by dropwise addition of 3.9 g of 1N NaOH. The neutralized resin powder A had a carboxyl group neutralization degree of 11.2%.

Preparation Example 3

82 g of butyl acrylate, 3 g of methacrylic acid, 15 g of ethylene glycol dimethacrylate, and 2 g of lauroyl peroxide were mixed and stirred in a beaker until dissolved. A solution of 0.75 g of sodium N-stearoyl-N-methyltaurine (SMT) in 400 g of ion-exchange water was added thereto, and the mixture was dispersed by using a homomixer until the particle size of oil droplet became 3.5 μm.

The dispersion was transferred into a four-necked flask, and the flask was purged and substituted with nitrogen for 30 minutes while the dispersion was stirred. The mixture in the flask was heated in an oil bath to a temperature of 80° C., allowed to polymerize at 80° C. for 5 hours, and then allowed to cool to room temperature. The polymerized particles were collected by freeze-drying the dispersion, to give a resin powder B.

Preparation Example 4

A neutralized resin powder B was prepared in a similar manner to Preparation Example 3, except that the dispersion containing polymerized particles in Preparation Example 3 was neutralized by dropwise addition of 3.9 g of 1N NaOH. The neutralized resin powder B had a carboxyl group neutralization degree of 11.2%.

Preparation Example 5

85 g of lauryl methacrylate, 15 g of ethylene glycol dimethacrylate, and 2 g of lauroyl peroxide were mixed and stirred in a beaker until dissolved. A solution of 0.75 g of sodium N-stearoyl-N-methyltaurine (SMT) in 400 g of ion-exchange water was added thereto, and the mixture was dispersed by using a homomixer until the particle size of oil droplet became 2.4 μm.

The dispersion was transferred into a four-necked flask, and the flask was purged and substituted with nitrogen for 30 minutes while the dispersion was stirred. The mixture in the flask was heated in an oil bath to a temperature of 80° C., allowed to polymerize at 80° C. for 5 hours, and then allowed to cool to room temperature. A resin powder C was obtained by freeze-drying the dispersion of the polymerized particles and collecting the particles.

Preparation Example 6

82 g of lauryl methacrylate, 3 g of methacrylic acid, 15 g of ethylene glycol dimethacrylate, and 2 g of lauroyl peroxide were mixed and stirred in a beaker until dissolved. A solution of 0.75 g of sodiumdodecyl sulfate(SDS) in 400 g of ion-exchange water was added thereto, and the mixture was dispersed by using a homomixer until the particle size of oil droplet became 2.5 μm.

The dispersion was transferred into a four-necked flask, and the flask was purged and substituted with nitrogen for 30 minutes while the dispersion was stirred. The mixture in the flask was heated in an oil bath to a temperature of 80° C., allowed to polymerize at 80° C. for 5 hours, and then allowed to cool to room temperature. The polymerized particles were collected by freeze-drying the dispersion, to give a resin powder D.

X-ray photoelectron spectroscopic (ESCA) analysis of the surfaces of the resin powders A, B, and C and the neutralized resin powders thereof obtained in Preparation Examples 1 to 5 revealed that the nitrogen atom only contained in sodium N-stearoyl-N-methyltaurine is present on the surface of the particles.

In addition, the average particle size and the compression strength of the resin powders A and B, neutralized resin powders thereof, and the resin powders C and D obtained in Preparation Examples 1 to 6 were determined according to the following methods, and the results are summarized in Table 1.

<Determination of Average Particle Size>

The median value of the particle size of each resin powder as determined by using a laser diffraction/scattering particle size distribution analyzer (model number: LA920, manufactured by Horiba, Ltd.) under the condition of a relative refractive index of 1.10 (assuming the refractive index of resin powder a 1.46 and that of water as 1.33) was designated as the average particle size.

<Determination of Compression Strength>

A resin particle was compressed under a constantly increasing load at 29 mgf/s up to 1 gf in a micro compression testing machine MCT-M200 manufactured by Shimadzu Corporation, and the compression strength was calculated according to the following equation, from the original particle size and the load when the particle size is deformed to an extent of 10%. The compression strength is the average of 10-sample measurements.

$$\text{Compression strength (kgf/mm}^2\text{)}=2.8\times\text{load (kgf)}/(\pi\times\text{particle size (mm)}\times\text{particle size (mm)})$$

TABLE 1

| | | | Average particle size (μm) | Compression strength (kgf/mm²) |
|---|---|---|---|---|
| Preparation example | 1 | Resin powder A | 2.2 | 5.0 |
| | 2 | Neutralized resinpowder A | 2.2 | 5.0 |
| | 3 | Resin powder B | 3.5 | 5.8 |
| | 4 | Neutralized resinpowder B | 3.5 | 5.8 |
| | 5 | Resin powder C | 2.4 | 1.6 |
| | 6 | Resin powder D | 2.5 | 5.0 |

Preparation Example 7

Poly(N-propionylethyleneimine)-modified silicone (component (d))

3.77 g (0.0244 mole) of diethyl sulfate and 48.4 g (0.488 mole) of 2-ethyl-2-oxazoline were dissolved in 107 g of dehydrated chloroform, and the mixture was refluxed under heat in a nitrogen environment for 5 hours, to give a terminal-active polymer of poly(N-propionylethyleneimine) (molecular weight: 2,000). A 50% ethyl acetate solution containing 400 g (0.0407 mole as amino group) of side-chain primary aminopropyl-modified dimethylsiloxane (molecular weight: 110,000, amine equivalent: 9,840) was added thereto all at once and the resulting mixture was refluxed under heat for 13 hours. The reaction mixture was concentrated under reduced pressure, to give a graft copolymer of polydimethylsiloxane having N-propionylethyleneimine chains (molecular weight: 137,000). The copolymer obtained was a pale yellow rubbery solid (yield: 444 g, 93%).

Examples of Cosmetic Sheet

Examples 1 to 6 and Comparative Examples 1 and 2

A 2 g pulp sheet (basis weight: 60 g/m²) was impregnated with 5 g of an aqueous dispersion having the composition shown in Table 2 by spraying, to give a cosmetic sheet. The impregnation rate of the aqueous dispersion was 250 weight %.

The cosmetic sheets obtained were evaluated by five professional panelists, who applied each of the sheets onto their forearms and rated the feeling in use concerning the following items according to the following criteria. Each sheet was ranked from the average of the scores by the five panelists according to the following criteria. Results are summarized in Table 2.

<Evaluation Item>
Nonstickiness
Score 4: nonsticky
Score 3: less sticky
Score 2: slightly sticky
Score 1: sticky
Nondryness
Score 4: not dry
Score 3: not much dry
Score 2: slightly dry
Score 1: dry
Durability of Nonstickiness (1 Hour After Application)
Score 4: retains nonstickiness
Score 3: retains some nonstickiness
Score 2: retains less nonstickiness
Score 1: retains no nonstickiness
<Criteria>
Average score: 3.5 to 4.0: ◉
Average score: 2.5 to 3.4: ○
Average score: 1.5 to 2.4: Δ
Average score: 1.0 to 1.4: ×

TABLE 2

|  |  | Example | | | | | | Comparative example | |
|---|---|---|---|---|---|---|---|---|---|
|  |  | 1 | 2 | 3 | 4 | 5 | 6 | 1 | 2 |
| Aqueous dispersion (%) | Resin powder A | 5 | 5 | — | — | — | — | — | — |
|  | Neutralized resin powder A | — | — | 5 | 5 | — | — | — | — |
|  | Resin powder C | — | — | — | — | 5 | — | — | — |
|  | Resin powder D | — | — | — | — | — | 5 | — | — |
|  | Talc | — | — | — | — | — | — | 5 | 5 |
|  | Neopentylglycol dicaprate | 1 | 1 | 1 | 1 | 1 | 1 | 1 | 1 |
|  | PEMULEN TR-1*[1] | 0.1 | 0.1 | 0.1 | 0.1 | 0.1 | 0.1 | 0.1 | 0.1 |
|  | Poly(N-acylalkyleneimine)-modified silicone*[2] | — | 0.5 | — | 0.5 | — | — | — | 0.5 |
|  | NaOH | 0.001 | 0.001 | 0.001 | 0.001 | 0.001 | 0.001 | 0.001 | 0.001 |
|  | Purified water | 93.899 | 93.399 | 93.899 | 93.399 | 93.899 | 93.899 | 93.899 | 93.399 |
|  | Total | 100.00 | 100.00 | 100.00 | 100.00 | 100.00 | 100.00 | 100.00 | 100.00 |
| Results of evaluation | Nonstickiness | ○ | ○ | ◉ | ◉ | ○ | ○ | Δ | Δ |
|  | Nondryness | ○ | ○ | ◉ | ◉ | Δ | ○ | × | × |
|  | Durability of nonstickiness | ○ | ◉ | ○ | ◉ | Δ | Δ | × | Δ |

*[1]Acrylic acid-alkyl methacrylate copolymer, manufactured by Noveon INC.
*[2]Sample obtained by preparation example 7

Example 7

A 2 g rayon/polyethylene (80/20) nonwoven fabric (basis weight: 50 g/m$^2$) was impregnated with 2 g of an aqueous dispersion having the following composition by spraying, to give a cosmetic sheet. The impregnation rate of the aqueous dispersion was 100 weight %. The cosmetic sheet obtained showed nonsticky, non-dry feeling, and retained its nonstickiness one hour after application.
<Aqueous Dispersion Composition>
Resin powder B 5.00%
Isopropyl myristate 2.00
Dimethyl silicone (10cs) 0.50
KF-6015*1 0.05
Polyoxyethylene hydrogenated castor oil*2 0.15
PEMULEN TR-1*3 0.10
Triethanolamine 0.10
Perfume 0.10
Ethanol 15.00
Purified water 77.00
Total 100.00
*1: Polyoxyethylene-methylpolysiloxane copolymer, manufactured by Shin-Etsu Chemical Co., Ltd
*2: EMANON CH-40, manufactured by Kao Corporation
*3: Acrylic acid-alkyl methacrylate copolymer, manufactured by Noveon Inc.

Example 8

A 1.5 g pulp/polyethylene (90/10) nonwoven fabric (basis weight: 50 g/m$^2$) was impregnated with 4 g of an aqueous dispersion having the following composition by spraying, to give a cosmetic sheet. The impregnation rate of the aqueous dispersion was 267 weight %. The cosmetic sheet obtained showed nonsticky, non-dry feeling, and retained its nonstickiness one hour after application.
<Aqueous Dispersion Composition>
Neutralized resin powder B 6.00%
Isopropyl palmitate 2.00
Oleic acid 0.10
Phellodenron Bark Extract 0.50
Carbopol ETD2020*1 0.15
Triethanolamine 0.15
Dibutylhydroxytoluene 0.02
Perfume 0.08
Ethanol 50.00
Purified water 41.00
Total 100.00
*1: Acrylic acid-alkyl methacrylate copolymer, manufactured by Noveon Inc.

Example 9

A 2g pulp/polyethylene (85/15) nonwoven fabric (basis weight 50 g/m$^2$) was impregnated with 5 g of an aqueous dispersion having the following composition by spraying, to give a cosmetic sheet. The impregnation rate of the aqueous dispersion was 250 weight %. The cosmetic sheet obtained showed nonsticky, non-dry feeling, and retained its nonstickiness one hour after application.
<Aqueous Dispersion Composition>
Neutralized resin powder B 5.00%
Neopentylglycol dicaprate 0.50
Monostearic acid polyoxyethylene(20) sorbitan 0.15
PEG400 (PEG-8 by INCI) 0.50
PEMULEN TR-1*1 0.15
Sodium carbonate 0.02

Perfume 0.06

Dibutylhydroxytoluene 0.02

Ethanol 25.00

Purified water 68.60

Total 100.00

*1: Acrylic acid-alkyl methacrylate copolymer, manufactured by Noveon Inc.

Examples of Powder Spray Cosmetic Formulations

Examples (2)-1 to (2)-4 and Comparative Examples (2)-1 to (2)-2

Powder spray cosmetic formulations having the compositions shown in Table 3 were prepared, and the powder spray cosmetic formulations obtained were evaluated by five professional panelists, who applied each of the preparations onto their forearms by spraying and rated the feel in use concerning the following items according to the following criteria. Each preparation was ranked from the average of the scores by the five panelists according to the following criteria. Results are summarized in Table 3.

<Evaluation Item>
Nonstickiness

Score 4: nonsticky

Score 3: less sticky

Score 2: slightly sticky

Score 1: sticky

Nondryness

Score 4: not dry

Score 3: less dry

Score 2: slightly dry

Score 1: dry

Durability of Nonstickiness (1 Hour After Application)
Score 4: retains nonstickiness
Score 3: retains some nonstickiness
Score 2: retains less nonstickiness
Score 1: retains no nonstickiness
<Criteria>
Average score: 3.5 to 4.0: ⊚
Average score: 2.5 to 3.4: ○
Average score: 1.5 to 2.4: Δ
Average score: 1.0 to 1.4: ×

TABLE 3

|  |  | Example | | | | Comparative example | |
|---|---|---|---|---|---|---|---|
|  |  | ②-1 | ②-2 | ②-3 | ②-4 | ②-1 | ②-2 |
| Powder spray cosmetic (%) | Resin powder C | 3.0 | — | — | — | — | — |
|  | Resin powder D | — | 3.0 | — | — | — | — |
|  | Resin powder A | — | — | 3.0 | — | — | — |
|  | Neutralized resin powder A | — | — | — | 3.0 | — | — |
|  | Talc | — | — | — | — | 3.0 | — |
|  | KMP-590*1 | — | — | — | — | — | 3.0 |
|  | Isopropylmethylphenol | 0.1 | 0.1 | 0.1 | 0.1 | 0.1 | 0.1 |
|  | Neopentylglycol dicaprate | 1.0 | 1.0 | 1.0 | 1.0 | 1.0 | 1.0 |
|  | SH-245*2 | 5.9 | 5.9 | 5.9 | 5.9 | 5.9 | 5.9 |
|  | Propellant(LPG 0.2 MPa) | 90.0 | 90.0 | 90.0 | 90.0 | 90.0 | 90.0 |
|  | Total | 100.0 | 100.0 | 100.0 | 100.0 | 100.0 | 100.0 |
| Results of evaluation | Nonstickiness | ○ | ○ | ○ | ⊚ | Δ | ○ |
|  | Nondryness | ○ | ○ | ⊚ | ⊚ | × | × |
|  | Durability of nonstickiness | Δ | ○ | ○ | ⊚ | × | Δ |

*1Powder of a methylsiloxane network polymer (manufactured by Shin-Etsu Chemical Co., Ltd., compression strength: 12 kgf/mm$^2$, average particle size: 2 μm)
*2Decamethylcyclopentasiloxane (manufactured by Toray Dow corning silicone).

Example (2)-5

A powder spray cosmetic formulation having the following composition was prepared. The powder spray cosmetic formulation obtained made the skin nonsticky and not dry, and retained its nonstickiness one hour after application.
<Composition>
Resin powder C 3.50%
Neopentylglycol dicaprate 3.00
Dimethyl silicone (10 cs) 0.10
KF-6015*1 0.05
Polyoxyethylene-hydrogenated castor oil*2 0.30
Antiperspirant (LOCRON P*3) 2.00
Isopropylmethylphenol 0.02
Perfume 0.50
Decamethylcyclopentasiloxane 0.53
Propellant (LPG 0.15 MPa) 90.00
Total 100.00
*1: Polyoxyethylene-methylpolysiloxane copolymer, manufactured by Shin-Etsu Chemical Co., Ltd.
*2: EMANON CH-40, manufactured by Kao Corporation
*3: Aluminum hydroxychloride, manufactured by Clariant GmbH

Example (2)-6

A powder spray cosmetic formulation having the following composition was prepared. The powder spray cosmetic formulation obtained made the skin nonsticky and not dry, and retained its nonstickiness one hour after application.
<Composition>
Neutralized resin powder A 2.00%
Isopropyl palmitate 3.00
Oleic acid 0.10
Phellodendron Bark Extract 0.10
Dibutylhydroxytoluene 0.02
Perfume 0.03
SH3775 M*1 0.10
Triclosan 0.02
Octamethylcyclotetrasiloxane 4.63
Isopentane 10.00
Propellant (LPG 0.25 MPa) 80.00
Total 100.00
*1: Polyoxyethylene-methylpolysiloxane copolymer, manufactured by Toray Dow Corning Silicone Co., Ltd.

Example (2)-7

A powder spray cosmetic formulation having the following composition was prepared. The powder spray cosmetic formulation obtained made the skin nonsticky and not dry, and retained its nonstickiness one hour after application.
<Composition>
Neutralized resin powder A 1.70%
Antiperspirant (LOCRON P*1) 1.00
Isopropyl myristate 1.62
Dimethyl silicone (10cs) 0.10
Talc 0.20
SH3775 M*2 0.30
Perfume 0.05
Dibutylhydroxytoluene 0.02
Triclosan 0.01
Propellant (LPG 0.20 MPa) 95,00
Total 100.00
*1: Aluminum hydroxychloride, manufactured by Clariant GmbH
*2: Polyoxyethylene-methylpolysiloxane copolymer, manufactured by Toray Dow Corning Silicone Co., Ltd.

Examples of Gel Cosmetics

Examples (3)-1 to (3)-4 and Comparative Examples (3)-1 to (3)-2

Gel type ultraviolet-protecting body cosmetic formulations having the compositions shown in Table 4 were prepared; and each of the cosmetic formulations obtained were evaluated by five professional panelists, who applied the formulation onto their forearms and rated the feel in use concerning the following items according to the following criteria. Each formulation was ranked from the average of the scores by the five panelists according to the following criteria. Results are summarized in Table 4.
<Evaluation Item>
Sticky Feeling of the Skin
Score 4: not sticky
Score 3: less sticky
Score 2: slightly sticky
Score 1: sticky
Nondryness
Score 4: not dry
Score 3: less dry
Score 2: slightly dry
Score 1: dry
Durability of Non-Sticky Feeling of the Skin (1 Hour After Application) Score 4: retains nonstickiness
Score 3: retains some nonstickiness
Score 2: retains less nonstickiness
Score 1: retains no nonstickiness
<Criteria>
Average score: 3.5 to 4.0: ⊚
Average score: 2.5 to 3.4: ○
Average score: 1.5 to 2.4: △
Average score: 1.0 to 1.4: ×

TABLE 4

|  |  | Example | | | | Comparative example | |
|---|---|---|---|---|---|---|---|
|  |  | ③-1 | ③-2 | ③-3 | ③-4 | ③-1 | ③-2 |
| Gel cosmetic (%) | Resin powder C | 8.00 | — | — | — | — | — |
|  | Resin powder D | 13 | 8.00 | — | — | — | — |
|  | Resin powder A | — | — | 8.00 | — | — | — |
|  | Neutralized resin powder A | — | — | — | 8.00 | — | — |
|  | Talc | — | — | — | — | 8.00 | — |
|  | KMP-590*1 | — | — | — | — | — | 8.00 |
|  | PEMULEN TR-2*2 | 0.30 | 0.30 | 0.30 | 0.30 | 0.30 | 0.30 |
|  | 2-amino-2-methyl-1-propanol | 0.15 | 0.15 | 0.15 | 0.15 | 0.15 | 0.15 |
|  | 2-ethylhexyl paramethoxycinnamate | 8.00 | 8.00 | 8.00 | 8.00 | 8.00 | 8.00 |

TABLE 4-continued

|  |  | Example ③-1 | Example ③-2 | Example ③-3 | Example ③-4 | Comparative example ③-1 | Comparative example ③-2 |
|---|---|---|---|---|---|---|---|
|  | Monostearic acid polyoxyethylene sorbitan (Ethylene oxide 20 mole adduct) | 0.10 | 0.10 | 0.10 | 0.10 | 0.10 | 0.10 |
|  | Ethanol | 40.00 | 40.00 | 40.00 | 40.00 | 40.00 | 40.00 |
|  | Purified water | 43.45 | 43.45 | 43.45 | 43.45 | 43.45 | 43.45 |
|  | Total | 100.00 | 100.00 | 100.00 | 100.00 | 100.00 | 100.00 |
| Results of evaluation | Nonsticky feeling of the skin | ○ | ◎ | ◎ | ◎ | ○ | ○ |
|  | Nondryness | ○ | ○ | ◎ | ◎ | X | X |
|  | Durability of nonstickiness | ○ | ○ | ○ | ◎ | Δ | ○ |

*[1]Powder of a methylsiloxane network polymer (manufactured by Shin-Etsu Chemical Co., Ltd., compression strength: 12 kgf/mm$^2$, average particle size: 2 μm)
*[2]Acrylic acid-alkyl methacrylate copolymer (manufactured by Noveon Inc.)

Example (3)-5

A gel type UV-protecting cosmetic formulation having the following compositions was prepared. The cosmetic formulation obtained did not make the skin sticky or dry and retained its nonstickiness 1 hour after application.
<Composition>
Resin powder D 6.00%
PEMULEN TR-2*1 0.20
Carbopol ETD2020*2 0.20
2-Ethylhexyl paramethoxycinnamate 5.00
Triethanolamine 0.20
Ethanol 40.00
Purified water 48.40
Total 100.00
*1: Acrylic acid-alkyl methacrylate copolymer, manufactured by Noveon Inc.
*2: Acrylic acid-alkyl methacrylate copolymer, manufactured by Noveon Inc.

Example (3)-6

A gel deodorant formulation having the following composition was prepared. The gel deodorant formulation obtained did not make the skin sticky or dry and retained its nonstickiness 1 hour after application.
<Composition>
Resin powder C 4.50%
Isopropylmethylphenol 0.20
PEMULEN TR-1*1 0.20
Triethanolamine 0.20
Neopentylglycol dicaprate 0.50
Perfume 0.02
Ethanol 60.00
Purified water 34.38
Total 100.00
*1: Acrylic acid-alkyl methacrylate copolymer, manufactured by Noveon Inc.

Example (3)-7

A gel whitening formulation having the following composition was prepared. The formulation obtained did not make the skin sticky or dry and retained its nonstickiness 1 hour after application.
<Composition>
Neutralized resin powder A 4.00%
L-Ascorbic acid-2-glucoside 2.00
PEMULEN TR-2*1 0.50
Sodium hydroxide 0.40
Glycerin 5.00
Propylene glycol 2.00
Monostearic acid polyoxyethylene(20) sorbitan 0.20
Octyldodecyl myristate 0.30
Ethanol 5.00
Purified water 80.60
Total 100.00
*1: Acrylic acid-alkyl methacrylate copolymer, manufactured by Noveon Inc.

Examples of Two Phase Separable Cosmetic

Examples (4)-1 to (4)-4 and Comparative Examples (4)-1 and (4)-2

Two-phase separation skin lotion having the compositions shown in Table 5 were prepared. The cosmetic formulations obtained were evaluated by five professional panelists, who applied each of the formulations onto their forearms and rated feel in use concerning the following items according to the following criteria. Each formulation was ranked from the average of the scores by the five panelists according to the following criteria. Results are summarized in Table 5.
<Evaluation Item>
Skin Smoothness
Score 4: smooth
Score 3: slightly smooth
Score 2: not much smooth
Score 1: not smooth
Nondryness
Score 4: not dry
Score 3: not much dry
Score 2: slightly dry
Score 1: dry
Durability of Skin Smoothness (1 Hour After Application)
Score 4: retains skin smoothness
Score 3: retains some skin smoothness
Score 2: retains less skin smoothness
Score 1: retains no skin smoothness
<Criteria>
Average score: 3.5 to 4.0: ◎.
Average score: 2.5 to 3.4: ○
Average score: 1.5 to 2.4: Δ
Average score: 1.0 to 1.4: ×

TABLE 5

| | | Example ④-1 | Example ④-2 | Example ④-3 | Example ④-4 | Comparative example ④-1 | Comparative example ④-2 |
|---|---|---|---|---|---|---|---|
| Two phase separable cosmetic (%) | Resin powder C | 5.0 | — | — | — | — | — |
| | Resin powder D | — | 5.0 | — | — | — | — |
| | Resin poweder A | — | — | 5.0 | — | — | — |
| | Neutralized resin powder A | — | — | — | 5.0 | — | — |
| | Talc | — | — | — | — | 5.0 | — |
| | KMP-590*1 | — | — | — | — | — | 5.0 |
| | Neopentyl glycol dicaprate | 0.8 | 0.8 | 0.8 | 0.8 | 0.8 | 0.8 |
| | Propylene glycol | 0.2 | 0.2 | 0.2 | 0.2 | 0.2 | 0.2 |
| | Ethanol | 82.0 | 82.0 | 82.0 | 82.0 | 82.0 | 82.0 |
| | Purified water | 12.0 | 12.0 | 12.0 | 12.0 | 12.0 | 12.0 |
| | Total | 100.0 | 100.0 | 100.0 | 100.0 | 100.0 | 100.0 |
| Result of evaluation | Smoothness of the skin | ○ | ◎ | ◎ | ◎ | Δ | ○ |
| | Nondryness | ○ | ○ | ◎ | ◎ | X | X |
| | Durability of smoothness | ○ | ○ | ○ | ◎ | X | ○ |

*1 Powder of a methylsiloxane network polymer (manufactured by Shin-Etsu Chemical Co., Ltd., compression strength: 12 kgf/mm$^2$, average particle size: 2 μm).

Example (4)-5

A two-phase separation skin lotion having the following composition was prepared. The skin lotion obtained made the skin smooth and not dry, and kept the skin smooth even one hour after application.
<Composition>
Resin powder A 1.00%
Ethanol 7.00
Glycerin 1.00
Phellodendron Bark Extract 0.50
1,3-Butylene glycol 0.20
Citric acid 0.10
Sodium citrate 0.10
Methyl paraoxybenzoate 0.10
Perfume 0.01
Polyethylene glycol monolaurate*1 0.01
Purified water 89.98
Total 100.00
*1: EMANON 1112 (manufactured by Kao Corporation).

Example (4)-6

A two-phase separation pump spray skin lotion having the following composition was prepared. The skin lotion obtained made the skin smooth and not dry, and kept the skin smooth even one hour after application.
<Composition>
Resin powder D 2.000%
Polyoxyethylene isocetylether (20EO) 0.500
Zinc paraphenolsulfonate 0.010
Glycerin 0.500
Polyethylene glycol 1540*1 1.000
High-molecular weight polyethylene glycol*2 0.001
1-Menthol 0.010
Disodium edetate 0.010
Methyl paraoxybenzoate 0.100
Ethanol 5.000
Purified water 90.869
Total 100.000
*1: PEG-1540 (PEG-32 by INCI, manufactured by Sanyo Chemical Industries, Ltd.)
*2: ALKOX E-100 (manufactured by Meisei Chemical Works. Ltd.).

Example (4)-7

A two-phase separation preshave lotion having the following composition was prepared. The preshave lotion obtained facilitated move of electric shaver during shaving, and provided favorable skin feeling, not dry, after shaving.
<Composition>
Neutralized resin powder A 5.0%
Neopentylglycol dicaprate 1.0
Isostearyl glyceryl ether 0.5
1,3-Butylene glycol 0.1
β-Glycyrrhetic acid 0.1
Perfume 0.3
Ethanol 81.0
Purified water 12.0
Total 100.0

Examples of Emulsion Cosmetic

Examples (5)-1 to (5)-4 and Comparative Examples (5)-1 and (5)-2

O/W emulsion cosmetic formulations having the compositions shown in Table 6 were prepared, and the cosmetic formulations obtained were evaluated by five professional panelists, who applied each of the formulations onto their forearms and rated feel in use concerning the following items according to the following criteria. Each formulation was ranked from the average of the scores by the five panelists according to the following criteria. Results are summarized in Table 6.
<Evaluation Item>
Sticky Feeling of the Skin
Score 4: not sticky
Score 3: less sticky
Score 2: slightly sticky
Score 1: sticky
Nondryness
Score 4: not dry
Score 3: not much dry
Score 2: slightly dry
Score 1: dry
Durability of Nonsticky Feeling of the Skin (1 Hour After Application)
Score 4: retains nonstickiness
Score 3: retains some unstickiness
Score 2: retains less unstickiness
Score 1: retains no unstickiness
<Criteria>
Average score: 3.5 to 4.0: ◎
Average score: 2.5 to 3.4: ○
Average score: 1.5 to 2.4: Δ
Average score: 1.0 to 1.4: ×

TABLE 6

|  |  | Example | | | | Comparative example | |
| --- | --- | --- | --- | --- | --- | --- | --- |
|  |  | ⑤-1 | ⑤-2 | ⑤-3 | ⑤-4 | ⑤-1 | ⑤-2 |
| Emulsion cosmetic (%) | Resin powder C | 5.0 | — | — | — | — | — |
|  | Resin powder D | — | 5.0 | — | — | — | — |
|  | Resin powder A | — | — | 5.0 | — | — | — |
|  | Neutralized resin powder A | — | — | — | 5.0 | — | — |
|  | Talc | — | — | — | — | 5.0 | — |
|  | KMP-590*1 | — | — | — | — | — | 5.0 |
|  | Stearic acid | 0.3 | 0.3 | 0.3 | 0.3 | 0.3 | 0.3 |
|  | Cetanol | 1.5 | 1.5 | 1.5 | 1.5 | 1.5 | 1.5 |
|  | Petrolatum | 1.0 | 1.0 | 1.0 | 1.0 | 1.0 | 1.0 |
|  | Liquid paraffin | 2.0 | 2.0 | 2.0 | 2.0 | 2.0 | 2.0 |
|  | Isododecane | 7.0 | 7.0 | 7.0 | 7.0 | 7.0 | 7.0 |
|  | Decamethylcyclopentasiloxane | 4.0 | 4.0 | 4.0 | 4.0 | 4.0 | 4.0 |
|  | Polyoxyethylene monooleic acid ester (Ethylene oxide 10 mole adduct) | 3.0 | 3.0 | 3.0 | 3.0 | 3.0 | 3.0 |
|  | Propylene glycol | 5.0 | 5.0 | 5.0 | 5.0 | 5.0 | 5.0 |
|  | Triethanolamine | 1.0 | 1.0 | 1.0 | 1.0 | 1.0 | 1.0 |
|  | Purified water | 70.2 | 70.2 | 70.2 | 70.2 | 70.2 | 70.2 |
|  | Total | 100.0 | 100.0 | 100.0 | 100.0 | 100.0 | 100.0 |
| Results of evaluation | Nonsticky feeling of the skin | ○ | ◎ | ◎ | ◎ | Δ | ○ |
|  | Nondryness | ○ | ○ | ◎ | ◎ | X | X |
|  | Durability of nonsticky feeling of the skin | ○ | ○ | ○ | ◎ | X | ○ |

*1Polymer of a methylsiloxane network polymer (manufactured by Shin-Etsu Chemical Co., Ltd., compression strength: 12 kgf/mm$^2$, average particle size: 2 μm).

Example (5)-5

An O/W emulsion having the following composition was prepared. The emulsion obtained was effective in suppressing a greasy feeling and the shininess of the skin for an extended period of time without giving a dry feeling.
<Composition>
Neutralized resin powder A 3.00%
PEMULEN TR-1*1 0.40
Sodium hydroxide 0.25
Tri(capryl-capric acid)glycerin 1.50
Alkyl (C12 to 15) benzoate 2.25
Polyethylene glycol monostearate 2.25
Polyoxyethylene(20) cetostearylether 0.38
Stearic acid 0.37
Dimethylpolysiloxane (10cs) 0.75
Ethanol 3.00
Propyl paraoxybenzoate 0.10
Methyl paraoxybenzoate 0.20
Perfume 0.02
1,3-Butylene glycol 3.00
Purified water 82.53
Total 100.00
*1: Acrylic acid-alkyl methacrylate copolymer, manufactured by Noveon Inc.

Example (5)-6

An O/W emulsion having the following composition was prepared. The emulsion obtained was effective in suppressing a greasy feeling and the shininess of the skin for an extended period of time without giving a dry feeling.
<Composition>
Resin powder A 2.00%
N-(Hexadecyloxyhydroxypropyl)-N-hydroxyethylhexadecanamide 3.00
Cholesterol 0.60
Cholesteryl isostearate 0.60
Stearic acid 0.30
Palmitic acid 0.30
Monoisostearic acid monomyristic acid glyceryl 0.80
Cetanol 0.75
Stearyl alcohol 0.50
Squalane 2.00
Neopentylglycol dicaprate 1.00
Dimethylpolysiloxane (6 cs) 3.00
Decamethylcyclopentasiloxane 3.00
Carbopol 980*1 0.15
Potassium hydroxide 0.04
Polyoxyalkylene laurylether sodium phosphate 0.90
Monostearic acid sorbitan 0.70
Polyoxyethylene-hydrogenated castor oil 0.70
Sodium N-Stearoyl-N-methyltaurine 0.20
Glycerin 3.00
1,3-Butylene glycol 2.00
Ethyl paraoxybenzoate 0.30
Butyl paraoxybenzoate 0.15
Ethanol 2.00
Perfume 0.01
Purified water 72.00
Total 100.00
*1: Carboxyvinyl polymer, manufactured by Noveon Inc.

Example (5)-7

A UV-protecting O/W emulsion having the following composition was prepared. The emulsion obtained was effective in suppressing a greasy feeling and the shininess of the skin for an extended period of time without giving a dry feeling.
<Composition>
Resin powder D 3.00%
Glyceryl monostearate 0.90
Stearic acid 0.50
Batyl alcohol 1.00
Isopropyl isostearate 1.00
Isopropyl myristate 2.00
2-Ethylhexyl paramethoxycinnamate 2.00
4-tert-Butyl-4'-methoxydibenzoylmethane 0.50
Octamethylcyclotetrasiloxane 2.00
Cholesterol 0.20

Carbopol 981*1 0.12
1,3-Butylene glycol 5.00
Disodium edetate 0.05
Potassium hydroxide 0.12
Ethanol 5.00
Methyl paraoxybenzoate 0.30
Propyl paraoxybenzoate 0.10
Butyl paraoxybenzoate 0.05
Perfume 0.05
Purified water 76.11
Total 100.00
*1: Carboxyvinyl polymer, manufactured by Noveon Inc.

Example (5)-8

A W/O cream formulation having the following composition was prepared. The cream obtained was effective in suppressing a greasy feeling and the shininess of the skin for an extended period of time without giving a dry feeling.
<Composition>
Resin powder C 10.00%
Microcrystalline wax 8.00
Light liquid paraffin 3.00
Light liquid isoparaffin 10.00
Beeswax 2.00
Vaseline 3.00
Octamethylcyclotetrasiloxane 12.00
Squalane 14.00
Isopropyl palmitate 10.00
Glyceryl monooleate 3.50
Polyoxyethylene(20) sorbitan monooleic acid ester 1.00
Methyl paraoxybenzoate 0.30
Propyl paraoxybenzoate 0.10
Propylene glycol 3.00
Perfume 0.10
Purified water 20.00
Total 100.00

Example (5)-9

An O/W whitening emulsion having the following composition was prepared. The emulsion obtained was effective in suppressing a greasy feeling and the shininess of the skin for an extended period of time without giving a dry feeling.
<Composition>
Neutralized resin powder A 3.50%
L-Ascorbic acid-2-glucoside 2.00
Glyceryl monostearate 0.90
Stearic acid 0.50
Batyl alcohol 1.00
Isopropyl isostearate 1.00
Isopropyl myristate 2.00
Octamethylcyclotetrasiloxane 2.00
Cholesterol 0.20
Carbopol 980*1 0.12
1,3-Butylene glycol 5.00
Disodium edetate 0.05
Potassium hydroxide 0.12
Ethanol 5.00
Methyl paraoxybenzoate 0.30
Propyl paraoxybenzoate 0.10
Butyl paraoxybenzoate 0.05
Perfume 0.05
Purified water 76.11
Total 100.00
*1: Carboxyvinyl polymer, manufactured by Noveon Inc.

Example (5)-10

A face-moisturizing emulsion having the following composition was prepared. The emulsion obtained was effective in suppressing a greasy feeling and the shininess of the skin for an extended period of time without giving a dry feeling.
<Composition>
Purified water 81.91%
1,3-Butylene glycol 3.00
PEMULEN TR-2*1 0.20
Carbopol ETD2020*2 0.15
Methyl paraoxybenzoate 0.20
Sodium hydroxide 0.25
Resin powder A 3.00
Tri(capryl-capric acid) glycerin 1.55
Alkyl (C12 to 15) benzoate 2.32
Glyceryl stearate 0.78
Polyethylene glycol monostearate 0.78
Polyoxyethylene cetostearyl ether (20EO) 0.39
Stearic acid 0.39
Dimethylpolysiloxane (10cs) 0.77
Fatty acid (C12-18) cetyl ester 1.16
Propyl paraoxybenzoate 0.10
Ethanol 3.00
Perfume 0.05
Total 100.00
*1: Acrylic acid-alkyl methacrylate copolymer, manufactured by Noveon Inc.
*2: Carboxyvinyl polymer, manufactured by Noveon Inc.

Example (5)-11

A UV-protecting face-moisturizing emulsion having the following composition was prepared. The emulsion obtained was effective in suppressing a greasy feeling and the shininess of the skin for an extended period of time without giving a dry feeling.
<Composition>
Purified water 76.55%
1,3-Butylene glycol 3.00
PEMULEN TR-1*1 0.20
Carbopol ETD2020*2 0.15
Methyl paraoxybenzoate 0.20
Sodium hydroxide 0.25
Neutralized resin powder A 3.00
Tri(capryl-capric acid)glycerin 0.50
Alkyl (12-15) benzoate 2.25
Glyceryl stearate 0.50
Polyethylene glycol monostearate 0.50
Polyoxyethylene cetostearyl ether (20EO) 0.25
Stearic acid 0.25
Dimethylpolysiloxane (10cs) 0.50
Fatty acid (C12-18) cetyl ester 0.75
2-Ethylhexyl paramethoxycinnamate 6.00
4-tert-Butyl-4'-methoxydibenzoylmethane 2.00
Propyl paraoxybenzoate 0.10
Ethanol 3.00
Perfume 0.05
Total 100.00

*1: Acrylic acid-alkyl methacrylate copolymer, manufactured by Noveon INC.
*2: Carboxyvinyl polymer manufactured by Noveon Inc.

Example (5)-12

A body care emulsion having the following composition was prepared. The emulsion obtained was effective in suppressing a greasy feeling and the shininess of the skin for an extended period of time without giving a dry feeling.
<Composition>
Purified water 76.10%
Glycerin 4.50
Methyl paraoxybenzoate 0.20
Neutralized resin powder A 5.00
Carbopol 981*1 0.10
Sodium hydroxide 0.10
Cetostearyl alcohol 1.60
Polyoxyethylene cetostearylether (20EO) 0.60
Cetyl alcohol 1.70
Fatty acid (C12-18) cetyl ester 2.20
Liquid lanolin 0.60
Glyceryl dilaurate 1.90
Propyl paraoxybenzoate 0.10
Dimethylpolysiloxane (200cs) 0.50
Ethanol 4.50
Perfume 0.30
Total 100.00
*1: Carboxyvinyl polymer, manufactured by Noveon Inc.

The invention claimed:

1. A cosmetic preparation comprising a crosslinked (meth) acrylic acid ester resin powder (a), said resin powder (a) having a compression strength of 2 to 8 kgf/mm$^2$, an average particle size of 1 to 10 μm and a spherical shape, wherein the resin powder (a) is prepared by copolymerization of monomer components containing at least one monomer selected from acrylic and methacrylic esters, and (meth)acrylic acid.

2. The cosmetic preparation according to claim 1, wherein the neutralization degree of the carboxyl groups in the resin powder of component (a) is 1 to 30%.

3. The cosmetic preparation according to claim 1, wherein the acrylic and methacrylic esters are acrylic and methacrylic alkyl esters having 1 to 18 carbon atoms in the alkyl group.

4. The cosmetic preparation according to claim 1, wherein the acrylic and methacrylic esters are present in an amount of 30 to 98 weight %, based on all monomer components.

5. The cosmetic preparation according to claim 1, wherein the copolymerization is carried out in the presence of a crosslinker.

6. A cosmetic sheet, prepared by impregnating a sheet-shaped substrate with an aqueous dispersion containing the cosmetic preparation according to claim 1 and an oil (b).

7. The cosmetic sheet according to claim 6, wherein the aqueous dispersion further contains a polymer dispersant as component (c).

8. The cosmetic sheet according to claim 6 or 7, wherein the aqueous dispersion further contains a poly(N-acylalkyleneimine)-modified silicone as component (d).

9. A powder spray cosmetic, comprising the cosmetic preparation according to claim 1.

10. A gel cosmetic, comprising the cosmetic preparation according to claim 1.

11. The gel cosmetic according to claim 10, which is an ultraviolet-protecting cosmetic preparation.

12. A two phase separable cosmetic comprising preparation according to claim 1 and a liquid medium.

13. An emulsion cosmetic, comprising the cosmetic preparation according to claim 1.

14. A method comprising applying the cosmetic preparation according to claim 1 to the skin.

* * * * *